United States Patent [19]

Mitra et al.

[11] Patent Number: 4,543,210

[45] Date of Patent: Sep. 24, 1985

[54] PROCESS FOR PRODUCING A HIGH PURITY ANTIHEMOPHILIC FACTOR CONCENTRATE

[75] Inventors: Gautam Mitra, Kensington; Paul K. Ng, Hercules, both of Calif.

[73] Assignee: Miles Laboratories, Inc., Elkhart, Ind.

[21] Appl. No.: 658,081

[22] Filed: Oct. 4, 1984

[51] Int. Cl.$^4$ .............. C07G 7/00; A61K 35/14; A61K 35/16; A23J 1/06
[52] U.S. Cl. ................... 260/112 B; 424/101
[58] Field of Search ............... 260/112 B; 424/101, 424/177

[56] References Cited

U.S. PATENT DOCUMENTS

| | | | |
|---|---|---|---|
| Re. 29,698 | 7/1978 | Fekete et al. | 260/112 B |
| 3,415,804 | 12/1968 | Polson | 260/112 B |
| 3,631,018 | 12/1971 | Shanbrom et al. | 260/112 B |
| 3,652,530 | 3/1972 | Johnson et al. | 260/112 B |
| 3,682,881 | 8/1972 | Fekete et al. | 260/112 B |
| 4,069,216 | 1/1978 | Shanbrom | 260/112 B |
| 4,104,266 | 8/1978 | Wickerhauser | 260/112 B |
| 4,170,639 | 10/1979 | Liu et al. | 424/101 |
| 4,188,318 | 2/1980 | Shanbrom | 260/112 B |
| 4,203,891 | 5/1980 | Rock | 260/112 B |
| 4,210,580 | 7/1980 | Amrani | 260/112 B |
| 4,289,691 | 9/1981 | Rock et al. | 260/112 B |
| 4,294,826 | 10/1981 | Feidman | 424/101 |
| 4,348,315 | 9/1982 | Blömbäck et al. | 260/112 B |
| 4,359,463 | 11/1982 | Rock | 424/101 |
| 4,383,989 | 5/1983 | Rock | 424/101 |
| 4,386,068 | 5/1983 | Mitra et al. | 424/101 |
| 4,387,092 | 6/1983 | Liautavd et al. | 424/101 |
| 4,404,131 | 9/1983 | Schwarz et al. | 260/112 B |
| 4,435,318 | 3/1984 | Pabst et al. | 260/112 B |
| 4,486,410 | 12/1984 | Fisher | 424/101 |
| 4,495,175 | 1/1985 | Chavin et al. | 424/101 |

FOREIGN PATENT DOCUMENTS 8307101 10/1983 Spain .

*Primary Examiner*—Howard E. Schain
*Attorney, Agent, or Firm*—Lester E. Johnson

[57] ABSTRACT

There is disclosed an improved process for producing high purity antihemophilic factor concentrate from an antihemophilic factor-containing dispersion or solution isolated from blood plasma or a blood plasma fraction, wherein the improvement is in carrying-out two consecutive precipitations using a combination of precipitants in each precipitation, first a combination of 1–4% by weight, based on weight of solution, of polyethylene glycol and 0.1–0.2 ml of 1–3%, based on weight of suspension, aluminum hydroxide suspension per gram of protein in the starting dispersion or solution, followed by a combination of added polyethylene glycol to provide a final concentration of 9–13% by weight, based on weight of the resulting solution, and 10–20% by weight of glycine, based on weight of the polyethylene glycol solution, and 10–20% by weight, based on weight of the polyethylene glycol solution, of sodium chloride.

20 Claims, No Drawings

PROCESS FOR PRODUCING A HIGH PURITY ANTIHEMOPHILIC FACTOR CONCENTRATE

BACKGROUND OF THE INVENTION

1. Field of the Invention

This invention relates to a process for producing a high purity antihemophilic factor (AHF) concentrate having improved specific activity and reduced amount of fibrinogen impurity from an AHF-containing dispersion by subjecting the dispersion to a multi-step purification using conventional precipitants including aluminum hydroxide gel, polyethylene glycol, and glycine with sodium chloride.

2. Description of the Prior Art

Polson, U.S. Pat. No. 3,415,804, defines a 4-step process for fractionating a mixture of proteinaceous substances by (1) mixing the proteinaceous substances with polyethylene glycol (PEG) in the presence of water to form a dispersion, the PEG-water dispersion being the only solvent phase present;

(2) adjusting the relative concentrations of proteinaceous substances and remaining components in the mixture in step (1) to a pH and temperature to effect separation of a protein phase and an aqueous liquid phase containing water and the remaining components of the mixture;

(3) separating said protein phase and said aqueous liquid phase from step (2); and (4) recovering a proteinaceous fractionation product from at least one of said fractions from step (3).

The polyethylene glycol suitable for use in the patented process has a molecular weight in the range of 300-100,000, preferably 600-20,000, more preferably 1,500-20,000, for example, 6,000. Polson also discloses well known variation of other parameters, such as, for example, to adjust the pH close to the isoelectric point of the protein component and to lower the ionic concentration and increase or lower temperature to increase separation of protein components, may be used in the patented process to have the same effect.

Shanbrom et al, U.S. Pat. No. 3,631,018, discloses an improved method of preparing a concentrate of AHF wherein the improvement is fractionating a cryoprecipitate concentrate of AHF with both polyethylene glycol and glycine in a three-step precipitation, (1) first with about 3-4% by weight of polyethylene glycol followed by recovery of the supernate;

(2) then with polyethylene glycol added to about 10% by weight followed by recovery of the resulting precipitate; and (3) finally with 1.3-1.8 M glycine added to a solution of the precipitate from step (2) followed by recovery of the resulting precipitate.

The polyethylene glycol suitable for use in the patented method has a molecular weight in the range of 200-20,000, preferably 400-6,000, more preferably about 4,000. The patent does not teach any ranges of limitations with respect to temperature and pH. However, Example 4 in the patent illustrates carrying out the precipitations at room temperature and at a pH of 6.5-6.88.

Johnson et al, U.S. Pat. No. 3,652,530, disclose a method of preparing highly purified AHF by treating an extract of a precipitate obtained by cryoethanol precipitation with polyethylene glycol in three successive precipitations, first with aluminum hydroxide gel at pH 5.6-7.0, then with polyethylene glycol to a concentration of 3.0-6.5%, and finally with added polyethylene glycol to a concentration of 10-12% to obtain a precipitate containing the highly purified AHF.

Fekete et al, U.S. Pat. No. 3,682,881, disclose a method for the preparation of a prothrombin complex and an AHF concentrate from citrated blood plasma treated with 1.5-1.8 M glycine. The resulting precipitate was treated successively with polyethylene glycol, first to a concentration of 3-4% and then 10% by weight, and finally with 1.8 M glycine.

Schwarz et al, U.S. Pat. No. 4,404,131, disclose an improved method of producing a F. VIII concentrate by subjecting a F. VIII concentrate obtained by conventional fractionation, e.g. cryoprecipitation, to cryoalcohol precipitation.

Fekete et al, U.S. Pat. No. Re. 29,698, disclose a method for improving the yield of AHF obtained from blood plasma and blood plasma fractions, obtained by cryoprecipitation, by the addition of heparin. The heparin-treated cryoprecipitate may then be further fractionated using polyethylene glycol and glycine. When the heparin-treated cryoprecipitate is further fractionated, heparin is preferably added twice, once to the initial cryoprecipitate and subsequently to the further fractionated concentrate.

Shanbrom, U.S. Pat. No. 4,069,216, discloses an improvement in the process disclosed in Shanbrom et al, U.S. Pat. No. 3,631,018 mentioned above, wherein the improvement is the step of holding a buffered solution of F. VIII and 6% polyol at 0°-5° C. until precipitation occurs.

Mitra et al, U.S. Pat. No. 4,386,068, disclose a process for producing an AHF concentrate by treating an aqueous suspension of cryoprecipitate containing AHF proteins with aluminum hydroxide gel, subjecting the resulting solution to ultrafiltration, and then constituting the solution resulting from the ultrafiltration in buffer and saline. Optionally, the solution resulting from the ultrafiltration may be treated with 1.6-2.2 M glycine for further purification.

Blomback et al, U.S. Pat. No. 4,348,315, disclose a process for purifying and/or concentrating the F. VIII complex, starting from cryoprecipitate or Cohn Fraction I-O, by dissolving a composition containing F. VIII together impurities in 1.5 M glycine solution at 15° C. and pH 6.3-7.8 to obtain a solution containing F. VIII and a precipitate containing the impurities. Optionally, the patented process includes the additional step of adding PEG to the resulting F. VIII-containing glycine solution followed by precipitating and then concentrating purified F. VIII from the solution.

Rock, U.S. Pat. No. 4,203,891, discloses a method of increasing the yield of antihemophilic factor VIII (AHF), from whole blood, blood plasma or blood plasma fractions by collecting the blood or plasma or plasma fraction from a donor directly into an anticoagulant agent selected from heparin, sodium heparin, or mixtures thereof, which agent does not reduce the physiological concentration of calcium, and recovering the AHF. Preferably, the anticoagulant is used in the range of 0.1-10 units/ml based on total volume of whole blood or blood plasma and the AHF is recovered by fractionation using glycine, ethanol, ethanolglycine, polyethylene glycol or glycine-polyethylene glycol precipitation.

Rock et al, U.S. Pat. No. 4,289,691, discloses a method for obtaining AHF from fresh blood plasma by adding heparin, used in the range of about 1-10 units/ml of plasma, to fresh plasma collected by plasmapheresis into a calcium chelating anticoagulant, freezing the plasma, resolubilizing the plasma, isolating a cryoprecipitate from the plasma, resolubilizing the cryoprecipitate, adding a citrate saline heparin buffer to the resolubilized cryoprecipitate, incubating the resolubilized, buffered cryoprecipitate at about 0°-10° C. for a time in excess of about 1 hour in the presence of heparin precipitable cold insoluble globulin, separating an AHF rich precipitate and isolating AHF from the precipitate.

Amrani, U.S. Pat. No. 4,210,580, discloses a process for separating and isolating AHF and fibronectin from plasma by cryoprecipitation (0°-15° C.) in the presence of a sulfated mucopolysaccharide, e.g. heparin, to a concentration of about 0.15-0.25 mg/ml of plasma (approximately 22.5 to 37.5 units of heparin/ml of plasma). The resulting fibronectin precipitate is purified chromatographically and the heparin supernatant is mixed with an anion exchange resin such as DEAE cellulose with Heparasorb to remove heparin and to provide a supernatant having 90-95% of the original procoagulant activity.

Rock, U.S. Pat. No. 4,383,989, discloses a method of obtaining AHF by collecting freshly obtained plasma or plasma fractions directly into heparin, sodium heparin or mixtures thereof, in a proportion of about 6-8 units of heparin/ml of plasma, in the absence of a citrate buffer, and applying a cold incubation technique (0°-10° C.) using heparin precipitable cold insoluble globulin.

Fekete et al, U.S. Pat. No. Re. 29,698, discloses a method of improving the yield of AHF from plasma and plasma fractions by adding 0.01-10 units of heparin per ml of a concentrate of AHF obtained from the plasma or plasma fraction by cryoprecipitation.

Spain Pat. No. ES 8,307,101 (Derwent Abstract 84-025300/05) discloses a process to produce high purity AHF by the cold purification of cryoprecipitate, extraction of factor VIII in tris-hydrochloride buffer, deactivation of the prothrombin complex using heparin and selective precipitation of fibrinogen with polyethylene glycol. The resulting solution is treated with additional polyethylene glycol to obtain factor VIII containing cryoprecipitate at about 0°-2° C.

Although the processes for producing antihemophilic factor (also referred to as "AHF" and as "F. VIII") have provided some improvement in product quality, in terms of enhanced specific activity and purity, and also in yield or recovery of the product AHF, there remains a need for further process improvement to obtain an AHF concentrate in high yield and high purity with minimization of the reduction in AHF specific activity associated with prior art processes.

DESCRIPTION OF THE INVENTION

Summary of the Invention

This invention is the discovery that, by combining two or more protein precipitating agents which heretofore have been used alone in a single-step process or in separate and distinct steps in a multi-step process in the production of antihemophilic factor from plasma or a plasma fraction, within certain ranges of amounts and proportions of precipitating agents and starting antihemophilic factor containing starting materials, of pH, and of temperature of the medium, there may be obtained an antihemophilic factor product having enhanced specific activity of about 10 or greater, fibrinogen levels reduced to the range of 20 mg or less of fibrinogen per 1,000 antihemophilic factor units, and improved yield of antihemophilic factor relative to prior art processes.

Accordingly, in one aspect, this invention is an improved process for producing an antihemophilic factor concentrate in a highly purified form and in high yields and with enhanced retention of antihemophilic factor clotting activity by treating an antihemophilic factor-containing dispersion or solution, optionally and preferably also containing heparin or sodium heparin or mixture thereof, with antihemophilic factor protein precipitating agents selected from aluminum hydroxide gel, polyethylene glycol, and glycine in a multi-step purification process, the improvement comprising subjecting the antihemophilic factor-containing dispersion or solution to two successive precipitations using a combination of precipitating agents in each of the precipitations, first by adding to the dispersion or solution a combination of about 1-3% aluminum hydroxide gel with about 1-4% by weight, based on volume of antihemophilic factor-containing dispersion or solution, of polyethylene glycol under conditions of acidic pH and a temperature of about 5°-10° C. followed by discardal of the resulting precipitate and recovery of the resulting supernatant solution, and then with a combination of sufficient added polyethylene glycol to increase the polyethylene glycol concentration in the recovered solution to about 9-15% by weight, based on volume of supernatant solution from the first precipitation, with about 10-20% by weight, based on total volume of resulting solution, of glycine and about 10-20% (w/v), based on total volume of resulting solution, of sodium chloride under conditions of acidic pH and a temperature of about 5°-10° C. followed by discardal of the resulting supernatant solution and recovery of the resulting precipitate. The thus recovered precipitate contains the highly purified antihemophilic factor concentrate product.

In another aspect, this invention is a highly purified antihemophilic factor concentrate produced by the process according to the invention. The thus produced highly purified antihemophilic factor concentrate may be dissolved in conventional physiologically compatible aqueous buffer solutions to which there may be added, optionally, conventional pharmaceutical adjuvants to provide pharmaceutical preparations. The antihemophilic factor concentrates or pharmaceutical preparations thereof may be treated using conventional techniques and procedures to reduce or eliminate infectious microorganisms and to render then non-infective to patients treated with the concentrates or pharmaceutical preparations.

DETAILED DESCRIPTION OF THE INVENTION

As the starting material, there may be used plasma or a plasma fraction containing antihemophilic factor (AHF). Preferably, the starting material will be a plasma fraction, more specifically, an AHF-containing cryoprecipitate such as that produced according to processes described in Hershgold et al, *J. Lab. & Clin. Med.*, 67, 23 (1966), Hagen et al, U.S. Pat. No. 3,973,002, and Liu et al, U.S. Pat. No. 4,170,639. Cryoprecipitate is produced by thawing frozen fresh plasma at temperatures from about 2°-6° C., centrifuging the thawed plasma and collecting the solid residue-the cryoprecipitate. The cryoprecipitate is then solubilized by suspending it in water, aqueous buffer solution or aqueous saline solution, preferably water-for-injection (WFI), to obtain a dispersion or solution of the cryoprecipitate. The cryoprecipitate may be present in the aqueous solution at a concentration of from 1-80% (weight/volume or w/v), preferably about 2-50% (w/v), more preferably about 5-25% (w/v), and most preferably about 10-20% (w/v).

In a preferred embodiment, there may be used in the process the addition of heparin at one or more of the steps. In an aspect of this preferred embodiment, there may be added to the medium for dissolving the cryoprecipitate or to a solution or suspension of cryoprecipitate heparin or sodium heparin or mixtures thereof in the range of amounts of from about 10-200 units/ml of starting dispersion or solution, more preferably about 30-165 units/ml, especially preferably about 60 units/ml. The use of heparin as described herein in the process according to this invention affords increased yield and, generally, enhanced purity (expressed by the specific activity) of the product AHF.

As mentioned above, the antihemophilic factor protein precipitating agents used in the improved process according to this invention are well-known and have been used conventionally alone in single- or multiple-step operations to isolate and purify plasma proteins including antihemophilic factor. The aluminum hydroxide suspension used in the process according to this invention may be any reagent grade gel suspension of aluminum hydroxide in water. Generally, the aluminum hydroxide suspension used will be a suspension of about 1-3%, based on total weight of suspension, of aluminum hydroxide in water. The amount of aluminum hydroxide suspension used will be in the range to provide about 0.1 to 0.25 g of aluminum hydroxide suspension per 1 g of protein contained in the starting material.

The polyethylene glycol precipitant used is a high molecular weight polymer generally produced by reacting ethylene oxide with ethylene glycol or with water to obtain the polycondensation product having repeating oxyethylene groups between a terminal hydroxyl group and a terminal hydroxyethyl group. The polyethylene glycol, sometimes abbreviated "PEG", can range in molecular weight from about 200 to 20,000, preferably about 2,000 to 10,000, more preferably about 3,000 to 8,000, most preferably about 3,000 to 4,000. As an example of a polyethylene glycol product that is suitable for use in the process according to this invention and that is commercially available, there may be mentioned the product PEG 3550 sold by Union Carbide Corp.

In the first precipitation operation, there is combined with the 1-3% aluminum hydroxide suspension about 1-4% by weight, based on volume of antihemophilic factor-containing dispersion or solution, of polyethylene glycol. In the second precipitation operation, there is combined with about 10-20% by weight, based on total weight of resulting solution, of glycine and about 10-20% by weight, based on total volume of resulting solution, of sodium chloride, about 9-15% by weight, based on volume of supernatant solution from the first precipitation, of polyethylene glycol. The concentration of polyethylene glycol in the second precipitation operation may be adjusted to about 9-15% by adding to the aqueous-polyethylene glycol solution recovered from the first precipitation operation sufficient polyethylene glycol to obtain the 9-15% by weight polyethylene glycol concentration. Alternatively, the aqueous-polyethylene glycol solution recovered from the first precipitation operation may be subjected to ultrafiltration to obtain a solution containing about 9-15% polyethylene glycol, to which there may then be added the glycine and sodium chloride. Typical ultrafiltration membranes that may be used in this alternative operation are, Amicon TM PM 10 (10,000 daltons), Romicon TM PM 10 (10,000 daltons), and the like. (Amicon is a trademark of Amicon Corporation, Lexington, Mass.; Romicon is a trademark of Romicon Corporation, Woburn, Mass.). Suitable recirculation pumps which may be used in the ultrafiltration procedure include, by way of example, the Amicon LP-20 (Amicon Corporation) air pressure operated diaphragm pump and the Warren-Rupp Sandpiper pump (Model SA1-A-DB-1-SS) (Thomas and Associates, Corte Madera, Cal.).

As an example of a glycine product that is suitable for use in the process according to this invention and that is commercially available, there may be mentioned the product glycine sold by Ajinomoto Co., Inc., Tokyo, Japan.

Any reagent grade sodium chloride product may be used in the second precipitation operation, according to this invention, in combination with polyethylene glycol and glycine.

The entire process of the present invention includes the steps of:
(a) isolating an antihemophilic factor containing starting material selected from plasma and a plasma fraction;
(b) forming an aqueous solution of the isolated antihemophilic factor containing material from step (a), said solution optionally and preferably further having added thereto heparin or sodium heparin or mixtures thereof in the range of amounts of about 10-200 units/ml based on total volume of resulting solution, more preferably about 30-165 units/ml, especially preferably about 60 units/ml;
(c) performing a first plasma protein precipitation by adding to the solution of the antihemophilic factor containing material from step (b) a suspension containing about 1-3% by weight, preferably about 2-3% by weight, based on total weight of suspension, of aluminum hydroxide in water and about 1-4% (w/v), based on volume of solution from step (b), of polyethylene glycol, and adjusting the pH of the resulting mixture to about 6.6-6.8 and the temperature of the resulting mixture to about 5°-10° C. and agitating the resulting mixture for about 15 minutes;
(d) separating the precipitate and recovering the supernatant aqueous-polyethylene glycol solution resulting from step (c), for example, by a conventional centrifugation procedure;
(e) performing a second plasma protein precipitation by adjusting the polyethylene glycol concentration of the aqueous-polyethylene glycol solution from step (d) to about 9-15% (w/v), based on volume of solution from step (d), for example, by adding sufficient polyethylene glycol or by subjecting the aqueous-polyethylene glycol solution from step (d) to ultrafiltration, and further adding to the so-adjusted solution about 10-20% by weight, based on total volume of solution in step (e), of glycine and about 10-20% by weight, based on total volume of solution in step (e), of sodium chloride, and adjusting the pH of the resulting mixture to about 5.7-6.8 and the temperature of the resulting mixture to about 5°-10° C. and agitating the resulting mixture for about 15 minutes;

(f) separating the supernatant aqueous-polyethylene glycol solution and recovering the precipitate resulting from step (e), for example, by a conventional centrifugation procedure;

(g) washing the so-recovered precipitate, for example, by use of a sodium chloride-glycine buffer solution at about 2° C. and recovering the precipitate;

(h) dissolving the washed precipitate from step (g) in a suitable aqueous medium, for example, a citrate-sodium chloride-glycine buffer solution;

(i) subjecting the solution obtained in step (h) to sterile-filtration; and (j) freeze-drying the sterile-filtered solution from step (i) to obtain a dried, highly purified AHF product.

The pharmaceutical preparations comprising the product produced by the process of the invention may be treated using conventional procedures to kill or inactivate infections, microorganisms, or reduce and eliminate the infectivity of microorganisms and to render the preparations non-viral, particularly non-hepatitis, infective. The pharmaceutical preparations may be sterile-filtered, heat treated, chemically treated, subjected to ultraviolet radiation or treated on colloidal silica.

For example, the preparations, in wet or dry state (that is, as the liquid concentrate itself or freeze-dried), may be heated at temperatures of about 60° to 85° C. for a period of several minutes to several days as may be required, generally in the presence of a heat stabilizing agent. Suitable stabilizing agents include nonpolar anions with molecular weights greater than 80, sugars, reduced sugars, and amino acids.

Examples of suitable nonpolar anions include salts of carboxylates, hydroxycarboxylates and amino acids such as a sodium or potassium caprylate, caprate, oleate, laurate, valerate, acetylphenylalaninate, acetyleucinate, and acetyltryptophanate. Examples of suitable sugars include glucose, sucrose and maltose to name but a few, and examples of suitable reduced sugars include erythritol and mannitol. Examples of suitable amino acids include lysine, glysine, proline and glutamic acid to name but a few.

By way of example without limitation, suitable conventional known processes to reduce or eliminate infectious microorganisms and render the preparations non-viral infective include those disclosed in U.S. Pat. Nos. 3,041,242, 3,057,781, 3,227,626, 4,061,735, 4,137,307, 4,297,344, 2,705,230, 2,897,123, 3,284,301, 3,454,929, 4,379,085, 4,370,264, 4,440,679 and 4,424,206, and European Patent Publications Nos. 0058993, 0077870 and 0094611, and in references disclosed in the patents.

In a preferred embodiment, there may be used the method of pasteurizing a thermally sensitive, therapeutically active protein set forth in U.S. Ser. No. 451,645 filed Dec. 20, 1982 commonly-owned by the assignee of this application. According to the above-mentioned method as applied in the process according to the present invention, o the AHF product is first mixed in an aqueous medium with about 0.04–0.8 M of at least one amino acid selected from glycine, lysine, arginine and alanine with at least about 30%, preferably from about 54% to saturation, on a weight to volume basis of a compound selected from sugars and reduced sugars such as sucrose and erythritol, respectively, to name representative examples. Then, the mixture is heated at a temperature of about 60°–75° C. and at a pH of about 5.5–8.0 for at least about 10 hours.

The following examples illustrate but a few embodiments of the present invention and are not to be construed as limiting in scope. All parts and percentages are by weight and temperatures in degrees Celsius unless otherwise indicated.

EXAMPLE 1

Fresh cryoprecipitate, 400 g, was mixed with four volumes of water-for-injection at 20°–30° C. The the dissolved cryoprecipitate was added 64 ml of 2% Al(OH)$_3$ in water suspension (0.16 ml 2% Al(OH)$_3$ per gm of cryoprecipitate) and polyethylene glycol having a molecular weight of 3350 (PEG 3350, Union Carbide Corp.) (62 g) to obtain 3% PEG in the solution. The pH value was adjusted to 6.7±0.1 with 1 M acetic acid. The resulting solution was cooled to 9° C., and then centrifuged at 8500 rpm for 15 minutes. The precipitate was discarded and about 1850 ml of supernatant liquid was recovered. PEG 3350 (148 g) was added to the clarified supernatant to make the final PEG concentration 11%. From this solution the Factor VIII was precipitated by adding 13% glycine (w/v) (240.5 g) and 14% NaCl (w/v) (259 g) and maintaining the pH at about 5.7. The solution was cooled to 6° C. and centrifuged at 8500 rpm for 15 minutes. The resulting precipitate (about 30 g) was washed with glycine/NaCl buffer (13% glycine/14% NaCl aqueous solution) at 2° C., centrifuged at 8500 rpm for 15 minutes, and dissolved in about 400 g of citrate-NaCl-glycine buffer (aqueous solution containing 0.005 M sodium citrate, 0.13 M NaCl, and 0.1 M glycine, pH 7.2–7.4). The product could be sterile filtered and lyophilized by conventional means. After sterile filtration, there was thus obtained 400 g of solution of highly purified AHF product in citrate-NaCl-glycine buffer having a specific activity of 9 units/A$_{280}$, where the A$_{280}$ is the ultraviolet absorbance of protein at 280 cm$^{-7}$ and is a measure of the quantity of protein present; and units/ml of AHF procoagulant activity protein (F. VIII:C)=35.0.

COMPARISON EXAMPLE A

A comparison AHF product was prepared according to the method disclosed in U.S. Pat. No. 3,631,018 (Example 4) as follows:

Reagents

Citrated saline. One part 0.1 molar sodium citrate to four parts by weight 0.9 percent saline.

Glycine citrated saline. Sufficient glycine is added to the above citrated saline to make a 0.1 molar solution respective of glycine.

Buffered wash water. To distilled water add 1/100 volume of buffered citrate which is made by adjusting 0.5 molar sodium citrate with 0.5 molar citric acid to pH 6.88.

Acetic acid. Prepared both 1.0 normal and 0.1 normal aqueous solutions.

Glycine. Prepare 1.3 molar aqueous solution.

Procedure

To 120 g cryoprecipitate, glycine citrated saline was added, the amount being one-tenth the volume of plasma the cryoprecipitate represents. Dissolution was brought about by mixing the cryoprecipitate and 1500 ml of glycine citrated saline in a warm environment (room temperature, but not in excess of 30° C.).

The dissolved cryoprecipitate was adjusted to pH 6.5 with 0.1 normal acetic acid. Polyethylene glycol 4000 was added to the solution to make the PEG concentration 3.5 percent. The mixture was gently agitated at room temperature for ten minutes, and then centrifuged for fifteen minutes at 5000 r.p.m. The supernate was decanted and adjusted to pH 6.88 with 0.1 normal sodium hydroxide. Additional polyethylene glycol 4000 was added to the solution to make the i=final PEG concentration 10 percent. The mixture was gently agitated at room temperature for thirty minutes, and centrifuged at 5000 r.p.m. for one-half hour. The supernate was decanted and the precipitate was washed in cold water (2° C.). Spin washing was then carried out for five minutes at 5000 r.p.m. at a temperature of −4° C. The supernate was decanted and the precipitate was redissolved in citrated saline.

The redissolved precipitate was adjusted to pH 6.88 with 0.1 normal acetic acid and then reprecipitated with glycine by cooling the solution to a temperature of 6–10° C. and adding sufficient glycine to make the solution 1.8 M with respect to glycine. The mixture was agitated for 45–60 minutes at 2°–10° C. The glycine precipitate was washed and clarified, and then lyophilized.

The specific activity (Units/$A_{280}$) and the relative percent of various protein components, determined by known cellulose acetate electrophoresis procedures, of the highly purified AHF product of Example 1 and of the AHF product of comparison Example A were determined. The results are set forth in Tables 1 and 2 below.

In Tables 1 and 2, Alb=albumin; $\alpha_1$=alpha-1 globulin; $\alpha_2$=alpha-2 globulin; $\beta$=beta-globulin; $\phi$=fibrinogen; and $\gamma$=gamma-globulin.

TABLE 1

|  | Specific Activity | Relative % (average of 2 assays) | | | | | |
|---|---|---|---|---|---|---|---|
|  |  | Alb | $\alpha_1$ | $\alpha_2$ | $\beta$ | $\phi$ | $\gamma$ |
| Example 1 | 2.2 | 68.0 | 2.9 | 13.4 | 8.8 | 4.2 | 2.6 |
| Example A | 0.8 | 38.4 | 0.05 | 29.0 | 11.6 | 16.8 | 4.4 |

Table 1 shows the relative specific activity and protein distribution in the intermediate products following the first precipitation in Example 1 using the combination of Al(OH)$_3$ suspension and PEG 3350 (3%) and in Example A using PEG alone (3.5%). It will be noted that the intermediate from the process according to the invention possesses significantly different properties from those of the intermediate of the comparison prior art process.

TABLE 2

|  | Specific Activity | Relative % (average of 2 assays) | | | | | |
|---|---|---|---|---|---|---|---|
|  |  | Alb | $\alpha_1$ | $\alpha_2$ | $\beta$ | $\phi$ | $\gamma$ |
| Example 1 | 9 | 0 | 0 | 82.5 | 14.6 | 0 | 3.1 |
| Example A | 0.4 | 0 | 0 | 8.4 | 0 | 92 | 0 |

Table 2 shows the relative specific activity and protein distribution in the final product following the second precipitation in Example 1 using the combination of PEG (11%) and glycine (13%) and NaCl (14%) and following the second PEG (10%) and third (final) glycine preciprtation in Example A. It will be observed that the product of Example 1, representative of the process according to the present invention, possesses in excess of 20-fold greater specific activity and an entirely different protein distribution when compared with the comparison product of Example A, representative of the prior art process.

EXAMPLE 2

(a) Another preparation of highly purified AHF product was produced by following substantially the procedure described in Example 1, except that there was used 510 g of starting cryoprecipitate. To a solution of the cryoprecipitate in four volumes of water-for-injection at 20°–30° C. there was added 81.6 ml of 2% (Al(OH)$_3$ in water suspension and 79 g of PEG 3350 to obtain 3% PEG in the solution. The pH was adjusted to about 6.69 with 1 M acetic acid. The resulting solution was cooled to 8° C. and then filtered. The precipitate was discarded and about 2365 ml of supernatant solution was recovered. The resulting intermediate had the following properties: $A_{280}$=4.17; units/ml of AHF procoagulant activity protein (F. VIII:C)=12.2; specific activity=2.93. The supernatant solution was divided into 880 ml and 1500 ml portions. The 1500 ml portion was further processed as described in Examples 3 below.

(b) To the 880 ml of the supernatant solution recovered from the first protein precipitation described above was added 70 g of PEG 3350 to make the final PEG concentration 11%. The resulting solution was divided into two portions of 470 ml. One 470 ml portion was further processed as described in Comparison Example B below.

(c) To the other 470 ml portion of the solution containing 11% PEG was added 61.1 g of glycine (13% glycine) and 65.8 g of NaCl (14% NaCl). The pH of the resulting mixture was adjusted to 6.7, and the mixture was cooled to 6° C. and then centrifuged at 8500 r.p.m. for 15 minutes. The resulting precipitate was washed with glycine/NaCl buffer at 2° C., centrifuged at 8500 r.p.m. for 15 minutes, and dissolved in citrate-NaCl-glycine buffer. After sterile filtration, there was obtained a solution weighing 22.4 g. The resulting product had the following properties: $A_{280}$=10.9; F. VIII:C=128.4 units/ml; specific activity =11.8; and fibrinogen =13.1%.

COMPARISON EXAMPLE B

The 470 ml portion of the solution containing 11% PEG which was set aside for further processing in Example 2, part (b) was adjusted to pH 6.7, cooled to 6° C., and centrifuged at 8500 r.p.m. for 15 minutes. The resulting precipitate was washed with glycine-NaCl buffer at 2° C., centrifuged at 8500 r.p.m. for 15 minutes, and dissolved in citrate-NaCl-glycine buffer. After sterile filtration, there was obtained a solution weighing 22.3 g. The resulting product had the following properties: $A_{280}$=22.0; F. VIII:C=46.6 units/ml; specific activity=2.21; and fibrinogen=19.5%.

EXAMPLE 3

(a) The 1500 ml portion of the supernatant solution resulting from the first precipitation operation in Example 2, part (a) was subjected to ultrafiltration at 32.5° C. to remove water and reduce the volume 3.6-fold and to thereby obtain 415 ml of aqueous-PEG solution having a final PEG concentration of 10.5±0.5%. The resulting solution containing 10.5±0.5% PEG was cooled to 7° C. and divided into 210 ml and 200 ml portions. The 200 ml portion was further processed as described in Comparison Example C below.

(b) To the 210 ml portion of the solution containing 10.5±0.5% PEG was added 27.3 g of glycine (13% glycine) and 29.4 g of NaCl (14% NaCl). The pH of the resulting mixture was adjusted to 7.06, and the mixture was cooled to 9° C. and then centrifuged at 8500 r.p.m. for 15 minutes. The resulting precipitate was washed with glycine-NaCl buffer at 2° C., centrifuged at 8500 r.p.m. for 15 minutes, and dissolved in citrate-NaCl-glycine buffer. After sterile filtration, there was obtained a solution weighing 23.2 g. The resulting product had the following properties: $A_{280}=8.61$; F. VIII:C=113.6 units/ml; specific activity=13.2; and fibrinogen=27.7%.

COMPARISON EXAMPLE C

The 200 ml portion of the solution containing 10.5±0.5% PEG which was set aside for further processing in Example 3, part (a) was adjusted to pH 7.06, cooled to 7°-9° C., and centrifuged at 8500 r.p.m. for 15 minutes. The resulting precipitate was washed with glycine-NaCl buffer at 2° C., centrifuged at 8500 r.p.m. for 15 minutes, and dissolved in citrate-NaCl-glycine buffer. After sterile filtration, there was obtained a solution weighing 20.4 g. The resulting product had the following properties: $A_{280}=10.9$; F. VIII:C=4.4 units/ml; specific activity=0.4; and fibrinogen=33.6%.

EXAMPLE 4

To about 2.75 kg of solution of about 100 g of about 100 g of paste, or precipitate, containing AHF recovered from a second precipitation step according to Example 1 dissolved in citrate-NaCl-glycine buffer as described in Example 1 above, there was added glycine, lysine, CaCl$_2$ and sucrose to obtain a mixture containing 0.8 mol/L of glycine, 0.8 mol/L of lysine, 2.0 mmol/L of CaCl$_2$ and 1.2 g/ml of sucrose. The mixture was heated at 60° C. for 10 hours to pasteurize it and then diafiltered against citrate-NaCl-glycine buffer. After sterile filtration, there was obtained 2.55 kg of solution having the following properties: $A_{280}=3.91$; AHF procoagulant activity (VIII:C)=32.2 units/ml; and specific activity=8.26 units/$A_{280}$. (Procoagulant activity (F.VIII:C) was assayed by the one stage APTT test modified from the methods of Langdell et al, *J. Lab. Clin. Med.*, 41, 637 (1953) and Procter et al, *Am. J. Clin. Path.*, 36, 212 (1961)).

EXAMPLE 5

To about 250 ml of solution of paste, or precipitate, containing AHF, which was recovered from a second precipitation step according to Example 1 starting with 250 g of fresh cryoprecipitate using proportionately reduced amounts of reagents, dissolved in about 250 ml of citrate-NaCl-glycine buffer as described in Example 1 above, there was added albumin to obtain a solution containing 2.5 mg/ml of albumin. The AHF concentrate/albumin mixture was sterile filtered, aseptically filled into bottles and freeze-dried using conventional techniques. The freeze-dried AHF concentrate contained in the bottles was heated at 68° C. for 72 hours to pasteurize it. Then, the dried, heat-treated AHF concentrate was reconstituted in 10 ml of water-for-injection. The reconstituted, heat-treated AHF concentrate of a representative bottle had the following properties: protein content=3.00 mg/ml; F. VIII:C=23.8 units/ml; and specific activity=7.93 units/mg protein.

EXAMPLE 6

This example illustrates the further improvement achieved according to the embodiment of the present invention utilizing the addition of heparin to the solution of the starting material. By following substantially the procedure described in Example 1, highly purified AHF product was produced with heparin, introduced by incorporation of said heparin in the initial water in which the starting cryoprecipitate was dissolved, or without heparin under the conditions set forth in Table 3 below.

TABLE 3

| Ex. No. | Cryo (g) | Amount of Heparin (μ/ml) | Specific Activity (U/$A_{280}$) | % Yield of AHF Product |
|---|---|---|---|---|
| a[1] | 400 | 0 | 12.2 | 49.92 |
| b[1] | 400 | 0 | 18.5 | 52.20 |
| c[2] | 4,000 | 0 | 12.0 | 41.40 |
| d[2] | 4,200 | 0 | 10.0 | 59.86 |
| e[3] | 310 | 162 | 18.2 | 45.76 |
| f[4] | 11,000 | 162 | 9.8 | 53.51 |
| g[5] | 3,000 | 0 | 14.2 | 62.34 |
| h[5] | 3,000 | 60 | 9.4 | 73.16 |
| i[6] | 3,500 | 0 | 6.7 | 31.46 |
| j[6] | 3,350 | 60 | 12.0 | 51.17 |
| k[7] | 5,000 | 0 | 14.0 | 48.69 |
| l[7] | 5,000 | 60 | 11.7 | 66.67 |
| m[8] | 2,300 | 0 | 11.3 | 42.02 |
| n[8] | 2,350 | 60 | 16.4 | 61.76 | foot notes
[1] % yield is based on an average cryo yield of 8 g/L of plasma
[2] % yield is based on actual yield of cryo determined from plasma
[3] Heparin was added after adjustment of pH to 7
[4] Heparin was added before addition of Al(OH)$_3$ suspension
[5] Starting material was fresh cryo derived from plasma having a high titer of CMV
[6] Starting material was frozen cryo derived from plasma having a high titer of rabies virus
[7] Starting material was frozen cryo derived from plasma having a high titer of CMV
[8] Starting material was fresh cryo derived from plasma having a low titer of Pseudomonas.

The data in Table 3 illustrate that, in addition to the advantage according to the multi-step process of this invention wherein the highly purified AHF product provides for a reduction of fibrinogen level in the product relative to the level of fibrinogen in comparable product produced according to processes known heretofore, the overall yield improvement according to the multi-step process of this invention may be further improved by the addition of heparin in the process, for example, in the aqueous medium used to dissolve the cryoprecipitate or to a solution or suspension of cryoprecipitate. Although the data above show variation in specific activity that is not understood and does not allow identification of any pattern, the advantageous increase in yield, especially in larger scale preparations, and the reduction in fibrinogen levels make the variable, or even lower, specific activity acceptable.

The highly purified AHF product produced according to the embodiment of this invention using the addition of heparin or compositions thereof may be treated as described in Example 5 ("dry" heat treatment at 68° C. for 72 hours) or Example 4 ("wet" heat treatment at 60° C. for 10 hours) in the presence of 0.8 M glycine, 0.8 M lysine, 2.0 mmol of CaCL$_2$ and 1.2 g/ml of sucrose to pasteurize the product or composition. Representative samples of AHF produced using added heparin (60 μ/ml) as described above in Example 6 h were sterile filtered and "dry" heat treated as described in Example 5 to afford a final average percent yield of 80% based on the starting amount of AHF before heating in the "dry" heat treatment step. Representative samples of AHF produced using added heparin (60 μ/ml) as described in Example 6 h, j, l and n above were "wet" heat treated as described in Example 4 to afford a final average yield of 72% based on starting AHF before heating in the "wet" heat treatment step.

What is claimed is:

1. In a process for producing high purity antihemophilic factor concentrate having enhanced specific activity and reduced fibrinogen impurity by the steps of:
   (a) isolating an antihemophilic factor containing starting material selected from blood plasma and a blood plasma fraction;
   (b) forming a solution of the so-isolated antihemophilic factor containing starting material from step (a);
   (c) performing a first plasma protein precipitation by adding to the solution of the antihemophilic factor containing starting material from step (b) about 1-4% (w/v), based on volume of solution from step (b), of polyethylene glycol, and adjusting the pH of the resulting mixture to about 6.6-6.8 and the temperature of the resulting mixture to about 5-10° C., and agitating the resulting mixture for about 15 minutes;
   (d) separating the precipitate and recovering the supernatant aqueous polyethylene glycol solution resulting from step (c);
   (e) performing a second plasma protein precipitation by adjusting the polyethylene glycol concentration of the aqueous-polyethylene glycol solution from step (d) to about 9-15% (w/v), based on volume of solution from step (d), and adjusting the pH of the resulting mixture to about 5.7-6.8 and the temperature of the resulting mixture to about 5°-10° C. and agitating the resulting mixture for about 15 minutes; and
   (f) separating the supernatant aqueous-polyethylene glycol solution and recovering the precipitate from step (e);
   the improvement comprising
   (i) combining with the polyethylene glycol in the first precipitation in step (c) a suspension containing about 1-3% by weight, based on total weight of suspension, of aluminum hydroxide in water, the aluminum hydroxide suspension being used in the ratio of about 0.1-0.25 g of aluminum hydroxide suspension per 1 g of protein in the starting antihemophilic factor containing starting material, and
   (ii) combining with the polyethylene glycol in the second precipitation in step (e) about 10-20% by weight, based on total volume of solution in step (e), of glycine and about 10-20% by weight, based on total volume of solution in step (e), of sodium chloride.

2. The process of claim 1 wherein the blood plasma fraction containing antihemophilic factor isolated from blood plasma in step (a) is a cryoprecipitate.

3. The process of claim 1 wherein (i) the first precipitation in step (c) is performed using about 2-3% by weight of polyethylene glycol and about a 2-3% suspension of aluminum hydroxide in water in the ratio of about 0.15-0.2 g of aluminum hydroxide suspension per 1 g of protein of the starting blood plasma fraction and (ii) the second precipitation in step (e) is performed using polyethylene glycol to about 10-15% by weight, about 12-18% by weight of glycine, and about 12-18% by weight of sodium chloride.

4. The process of claim 2 wherein (i) the first precipitation in step (c) is performed using about 2-3% by weight of polyethylene glycol and about a 2-3% suspension of aluminum hydroxide in water in the ratio of about 0.15-0.2 g of aluminum hydroxide suspension per 1 g of protein of the starting blood plasma fraction and (ii) the second precipitation in step (e) is performed using polyethylene glycol to about 10-15% by weight about 12-18% by weight of glycine, and about 12-18% by weight of sodium chloride.

5. The process of claim 4 wherein (i) the first precipitation in step (c) is performed using about 3% by weight of polyethylene glycol and about a 3% suspension of aluminum hydroxide in water in the ratio of about 0.16 g of aluminum hydroxide suspension per 1 g of protein of the starting blood plasma fraction and (ii) the second precipitation in step (e) is carried out using polyethylene glycol to about 10-12% by weight, about 12-15% by weight of glycine and about 12-15% by weight of sodium chloride.

6. The process of claim 4 wherein (i) the first precipitation in step (c) is performed using about 3% by weight of polyethylene glycol and about a 3% suspension of aluminum hydroxide in water in the ratio of about 0.16 g of aluminum hydroxide suspension per 1 g of protein of the starting blood plasma fraction and (ii) the second precipitation in step (e) is carried out using polyethylene glycol to about 11% by weight, about 13% by weight of glycine and about 14% by weight of sodium chloride.

7. The process of claim 1 wherein there is added in at least one of steps (b) and (c) at least one of heparin, sodium heparin or mixtures thereof in the range of amounts of 10-200 units/ml of solution of suspension.

8. The process of claim 1 which further comprises the steps of solubilizing the recovered precipitate from step (f), sterile filtering the solubilized precipitate, and then freeze-drying the sterile-filtered solubilized precipitate.

9. The process of claim 6 wherein there is added in step (b) about 60 units/ml of at least one of heparin, sodium heparin or mixtures thereof.

10. The process of claim 6 which further includes the step of treating the sterile-filtered solubilized precipitate to reduce and eliminate infections microorganisms and to render the sterile-filtered solubilized precipitate non-hepatitis infective.

11. The process of claim 7 which further includes the step of treating the sterile-filtered solubilized precipitate to reduce and eliminate infections microorganisms and to render the sterile-filtered solubilized precipitate non-hepatitis infective.

12. The process of claim 8 which further includes the step of treating the sterile-filtered solubilized precipitate to reduce and eliminate infections microorganisms and to render the sterile-filtered solubilized precipitate non-hepatitis infective.

13. A high purity antihemophilic factor concentrate produced by the process of claim 1.

14. A high purity antihemophilic factor concentrate produced by the process of claim 2.

15. A high purity antihemophilic factor concentrate produced by the process of claim 6.

16. A high purity antihemophilic factor concentrate produced by the process of claim 7.

17. A high purity antihemophilic factor concentrate produced by the process of claim 8.

18. A high purity antihemophilic factor concentrate produced by the process of claim 10.

19. A high purity antihemophilic factor concentrate produced by the process of claim 11.

20. A high purity antihemophilic factor concentrate produced by the process of claim 12.

* * * * *